United States Patent [19]

Meyer et al.

[11] Patent Number: 5,152,922
[45] Date of Patent: Oct. 6, 1992

[54] 1,4-DISTYRYLBENZENE COMPOUNDS AND MIXTURES THEREOF WITH OTHER 1,4-DISTYRYBENZENE COMPOUNDS

[75] Inventors: Hans R. Meyer, Binningen; Leonardo Guglielmetti, Bottmingen, both of Switzerland

[73] Assignee: Ciba-Geigy Corporation, Ardsley, N.Y.

[21] Appl. No.: 671,178

[22] Filed: Mar. 15, 1991

Related U.S. Application Data

[63] Continuation of Ser. No. 411,186, Sep. 20, 1989, abandoned, which is a continuation of Ser. No. 64,740, Jun. 22, 1987, abandoned.

[30] Foreign Application Priority Data

Jul. 1, 1986 [CH] Switzerland ............... 2637/86

[51] Int. Cl.$^5$ ................................. C09K 11/06
[52] U.S. Cl. ................. 252/301.21; 568/28; 568/34; 568/36; 558/413; 558/420; 560/76; 252/301.22; 252/301.24; 252/301.25; 252/301.27; 252/301.29; 252/301.32
[58] Field of Search .......... 252/301.21, 301.22, 252/301.24; 260/400, 402.5, 404; 568/28, 34, 36; 570/184

[56] References Cited

U.S. PATENT DOCUMENTS

| | | | |
|---|---|---|---|
| 4,330,427 | 5/1982 | Martini et al. | 252/301.21 |
| 4,380,514 | 4/1983 | Seybold | 252/301.21 |
| 4,464,284 | 8/1984 | Seybold | 252/301.21 |

FOREIGN PATENT DOCUMENTS

| | | |
|---|---|---|
| 2929599 | 2/1981 | Fed. Rep. of Germany . |
| 3001066 | 7/1981 | Fed. Rep. of Germany . |
| 920988 | 3/1963 | United Kingdom . |
| 1045443 | 10/1966 | United Kingdom . |

OTHER PUBLICATIONS

Chemical Abstract 95:152101 pp. 71–72.
Chemical Abstract 104:150793 p. 96.

*Primary Examiner*—John Niebling
*Assistant Examiner*—Kathryn Gorgos
*Attorney, Agent, or Firm*—Marla J. Mathias; Edward McC. Roberts

[57] ABSTRACT

Novel 1,4-distyrylbenzene compounds of the formula

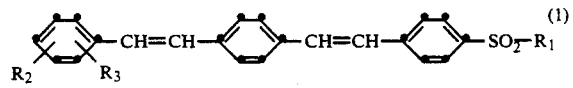

and mixtures thereof with compounds of the formulae

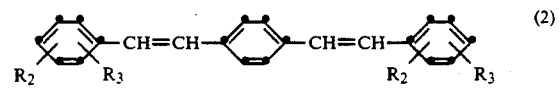

and/or

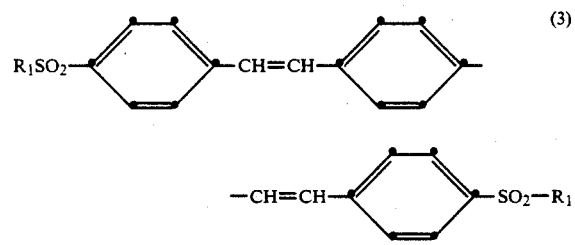

in which $R_1$ is $C_1$–$C_4$-alkyl or phenyl, $R_2$ is cyano, $COOC_1$–$C_4$-alkyl or chlorine and $R_3$ is hydrogen or chlorine, agents for the fluorescent brightening of polyester fibers and a process for the preparation of the compounds of the formula 1 or mixtures thereof with compounds of the formulae 2 and/or 3 and also novel aldehydes which can be isolated as intermediates.

7 Claims, No Drawings

1,4-DISTYRYLBENZENE COMPOUNDS AND MIXTURES THEREOF WITH OTHER 1,4-DISTYRYBENZENE COMPOUNDS

This application is a continuation of application Ser. No. 411,186, filed Sep. 20, 1989, now abandoned which is a continuation of application Ser. No. 064,740, filed Jun. 22, 1987, now abandoned.

The present invention relates to novel, asymmetrically substituted 1,4-distyrylbenzene compounds, mixtures thereof with symmetrically substituted 1,4-distyrylbenzene compounds, a process for the preparation of the abovementioned compounds or mixtures and agents for the fluorescent brightening of polyester fibers and to novel aldehydes formed as intermediates in the preparation of the abovementioned compounds.

Symmetrically substituted 1,4-distyrylbenzene compounds and processes for their preparation are described in DE-A 1,112,072, DE-A 1,444,003 and DE-A 2,401,665, whereas asymmetrically substituted 1,4-distyrylbenzene compounds and mixtures thereof with asymmetrically and/or symmetrically substituted 1,4-distyrylbenzene compounds and processes for the preparation thereof are already known from EP-A 30,917, EP-A 32,254, DE-A 3,339,383 and DE-A 3,347,576. A factor common to all of these is their use as fluorescent brighteners for polyester fibers in particular.

The novel, asymmetrically substituted 1,4-distyrylbenzene compounds are characterized by the formula

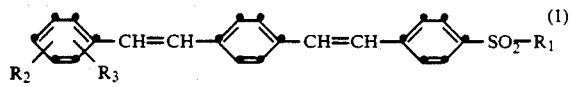

in which $R_1$ is $C_1$–$C_4$-alkyl or phenyl, $R_2$ is cyano, $COOC_1$ $C_4$-alkyl or chlorine and $R_3$ is hydrogen or chlorine.

Compared with the individual components of the formulae

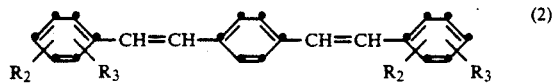

and/or

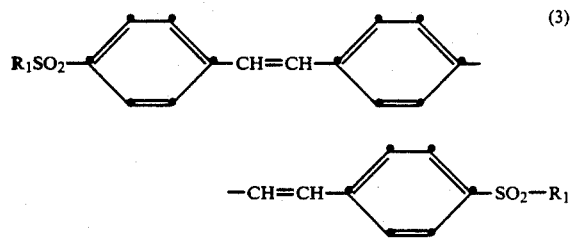

as fluorescent brighteners of polyester fibers or material containing polyester fibers, the novel compounds of the formula 1 and mixtures thereof with the symmetrically substituted 1,4-distyrylbenzene compounds of the formulae 2 and 3, some of which were previously known, exhibit an improved degree of whiteness, particularly at low fixing temperatures.

Preferred 1,4-distyrylbenzene compounds of the formula 1 are those in which $R_1$ is methyl or ethyl, $R_2$ is cyano or 4-chlorine and $R_3$ is hydrogen or, if $R_2$ is 4-chlorine, is 3-chlorine, and particularly those in which $R_1$ is methyl, $R_2$ is 2-cyano and $R_3$ is hydrogen.

Preferred mixtures of asymmetrical and symmetrical 1,4-distyrylbenzene compounds contain 1 to 99% by weight of 1-(2-cyanostyryl)-4-(4-methylsulfonylstyryl)-benzene or 1-(2-cyanostyryl)-4-(4-ethylsulfonylstyryl)-benzene, 1 to 99% by weight of 1,4-di-(2-cyanostyryl)-benzene and 0 to 20% by weight of 1,4-di-(4-methylsulfonylstyryl)-benzene or 1,4-di(4-ethylsulfonylstyryl)-benzene.

The present invention also relates to agents for the fluorescent brightening of polyester fibers or material containing polyester fibers which contain at least one of 1,4-distyrylbenzene compound of the formula

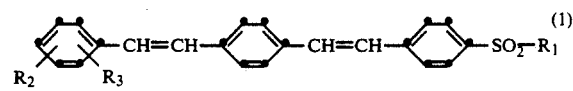

or a mixture thereof with at least one of the compounds of the formulae

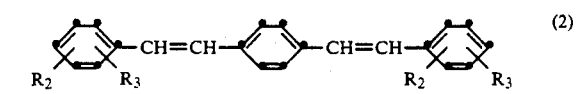

and/or

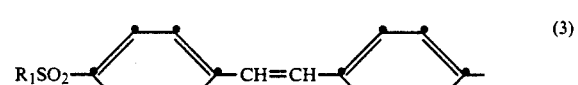

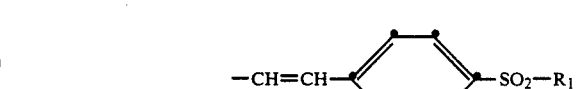

$R_1$ in the compounds of the formula 1 to 3 being $C_1$–$C_4$-alkyl or phenyl, $R_2$ being cyano, $COOC_1$–$C_4$-alkyl or chlorine and $R_3$ being hydrogen or chlorine.

In addition, the agents according to the invention can also contain one or more fluorescent brighteners known per se belonging to the series comprising 1,4-distyrylbenzenes, 4,4'-distyrylbiphenyls, 2,5-dibenzoxazolylthiophenes, 1,2-dibenzoxazolylethylenes, monobenzoxazolylstilbenes, monobenzoxazolylstyrenes, dibenzoxazolylstilbenes, dibenzoxazolylstyrenes, triazinylpyrenes, 4-triazolylstilbenes, isoxazolylstilbenes, dibenzoxazolylnaphthalenes, triazolylcoumarins, pyrazolylcoumarins, phenylcoumarins, 4,4'-divinylstilbenes and naphthalimides.

The preparation of the asymmetrically substituted 1,4-distyrylbenzene compounds, according to the invention, of the formula 1 or mixtures thereof with symmetrically substituted 1,4-distyrylbenzene compounds of the formulae 2 and/or 3 is effected by subjecting terephthaldehyde to a condensation reaction in one or two reaction stages with the two phosphonates of the formulae

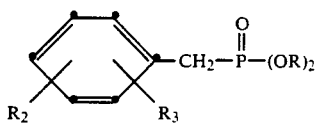

and

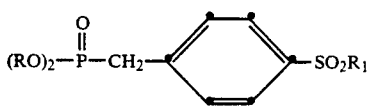

in which R is $C_1$–$C_4$-alkyl.

It is possible, if desired, to isolate the aldehydes of the formulae

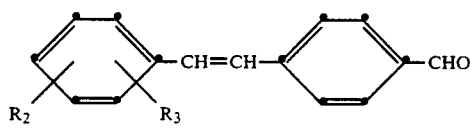

or

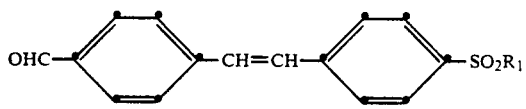

which are formed as intermediates in the condensation reaction of terephthaldehyde with the two phosphonates of the formulae 4 and 5. The aldehydes of the formulae 7 and

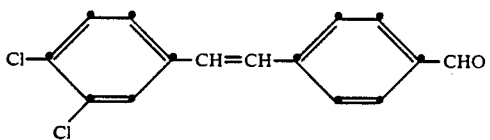

which can be isolated as intermediates are novel and are hence also claimed as novel compounds. Whereas in the preparation of the 1,4-distyrylbenzene compounds of the formula 1, one mol of terephthaldehyde is subjected to a condensation reaction with one mol in each case of the two phosphonates of the formulae 4 and 5 in 2 successive stages, in the preparation of mixtures of the compounds of the formula 1 with compounds of the formulae 2 and/or 3, the condensation reaction of terephthaldehyde with the two phosphonates of the formulae 6 and 7 is carried out in the stoichiometric ratios intended for each of the mixtures. The mixtures can also be prepared in a simple manner by mixing the compounds of the formula 1 with those of the formulae 2 and/or 3 without a diluent.

The agents according to the invention are excellently suitable for the fluorescent brightening of textile materials composed of linear or modified polyesters. As is customary in the case of fluorescent brighteners, the individual compounds can be dispersed in a liquid medium, for example water, and the dispersions can then be combined. It is also possible, however, to disperse the mixture obtainable from the above process of compounds of the formula 1 with compounds of the formulae 2 and/or 3, or a mixture of these individual compounds, jointly and without a diluent, which is effected in a customary manner in ball mills, colloid mills, bead mills or the like. The agents according to the invention can be applied to the textile material by known methods, for example by the exhaustion process at 90° to 140° C. or by the pad-bake process at 160° to 220° C. Application is advantageously carried out in an aqueous medium in which the compounds are present in a finely divided form as suspensions, so-called micro-dispersions or, if appropriate, solutions. Finally, it is also possible to add dispersing agents, stabilizers, wetting agents and other auxiliaries in the course of the application.

The following examples illustrate the invention.

EXAMPLE 1

An amount of 8.8 g of 30% methanolic sodium methylate solution are added dropwise at room temperature to a solution of 9.5 g of 4'-methylsulfonylstilbene-4-aldehyde and 9.5 g of diethyl 2-cyanobenzylphosphonate (97.2% strength) in 60 ml of dimethylformamide. The mixture is stirred for a further 2 hours at 40° C. and is cooled and 30 ml of water are added. The pale yellow mash of crystals is filtered off with suction and washed several times with methanol and water. Drying in vacuo gives 11.7 g of the compound of the formula

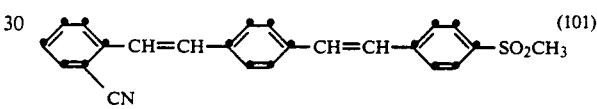

melting point 215°–216° C. after recrystallization from chlorobenzene and ethylene glycol monomethyl ether.

The 4'-methylsulfonylstilbene-4-aldehyde required is obtained as follows: 33.5 g of terephthalaldehyde are introduced, in portions, into a solution of 17.5 g of potassium hydroxide (88% strength) in 200 ml of methanol at room temperature and with stirring and cooling and also nitrogen blanketing. When the material has dissolved completely, a solution of 81.0 g of diethyl p-methylsulfonylbenzylphosphonate (94.5% strength, melting point 66°–68° C.) is added dropwise at 10° C. in the course of ¼ hour, in the course of which the reaction product begins to separate out. The suspension is stirred overnight at room temperature to complete the reaction and is cooled in an icebath and filtered, and the residue is washed several times with methanol and water. Drying in vacuo at 80° C. gives 65.7 g of the compound of the formula

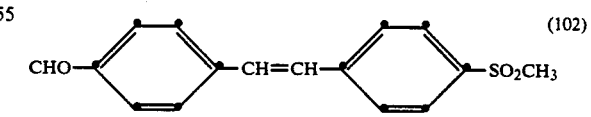

in the form of a pale yellow powder of melting point 188°–190° C. It can be recrystallized from xylene.

The diethyl p-methylsulfonylbenzylphosphonate is obtained by heating p-methylsulfonylbenzyl chloride with excess triethyl phosphite at 140°–145° C. and then distilling the mixture in a high vacuum: colorless, viscous oil which solidifies in the receiver, melting point 70°–72° C. (recrystallized from carbon tetrachloride).

EXAMPLE 2

An amount of 7.9 g of a 30% solution of sodium methylate in methanol are added dropwise at room temperature and with stirring and nitrogen blanketing, to a solution of 2.7 g of terephthalaldehyde, 4.1 g of 1-diethylphosphonomethyl-4-methylsulfonylbenzene (75% strength) and 7.8 g of 2-diethylphosphonomethylbenzonitrile in 20 ml of dimethylformamide. The mixture is stirred for a further 2 hours at 30°–40° C., cooled and diluted with 20 ml of methanol and 10 ml of water, and the precipitated product is filtered off with suction. Repeated washing with methanol and water and drying in vacuo at 80° C. gives 6.0 g of a pale yellow powder consisting of 38% by weight of the compound of the formula (101), 56% by weight of the compound of the formula

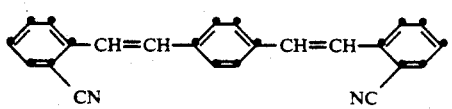
(103)

and 6% by weight of the compound of the formula

(104)

(content determined by means of high pressure liquid chromatography).

EXAMPLE 3

An amount of 5.2 g of a 30% methanolic sodium methylate solution are added dropwise at room temperature to a solution of 4.7 g of the compound of the formula

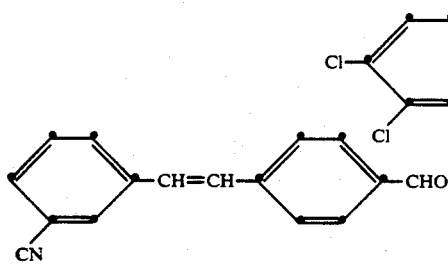
(105)

and 9.6 g of diethyl p-methylsulfonylbenzylphosphonate (70% strength) in 60 ml of dimethylformamide. The mixture is stirred for 2 hours at 40°–45° C. and is cooled, and 60 ml of water are added. The precipitated product is filtered off with suction, washed several times with methanol and water and dried in vacuo. This gives 6.1 g of the compound of the formula

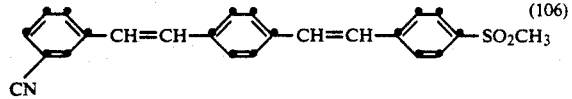
(106)

melting point 226°–227° C. after recrystallization from chlorobenzene and ethylene glycol monomethyl ether.

EXAMPLE 4

An amount of 3.3 g of sodium methylate are added to a solution of 22.8 g of the compound of the formula

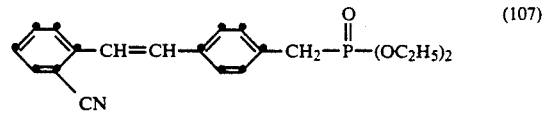
(107)

and 7.2 g of p-methylsulfonylbenzaldehyde in 100 ml of dimethylformamide. The suspension is stirred for 3 hours at 45° C. and is allowed to cool, and water is added. The precipitated product is filtered off with suction and washed several times with alcohol and water. An amount of 12.0 g of the compound of the formula (101) are obtained. Melting point 217°–218° C. (from chlorobenzene).

The compound of the formula (107) which is required as the starting material is obtained, for example, by brominating 2-cyano-4'-methylstilbene with N-bromosuccinimide in boiling carbon tetrachloride in the presence of dibenzoyl peroxide, and then reacting the resulting 4-bromomethyl-2'-cyanostilbene (melting point 120°–122°) with excess triethyl phosphite at 140° C.

EXAMPLE 5

The procedure described in Example 1 is repeated, using the corresponding amount of diethyl 3,4-dichlorobenzylphosphonate, added dropwise at 40° C., instead of diethyl 2-cyanobenzylphosphonate. The compound of the formula

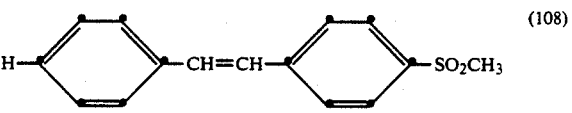
(108)

is obtained in the form of pale yellow crystals of melting point 264°–265° C. (recrystallized from chlorobenzene).

Conversely, the compound of the formula (108) is also obtained by subjecting the aldehyde of the formula

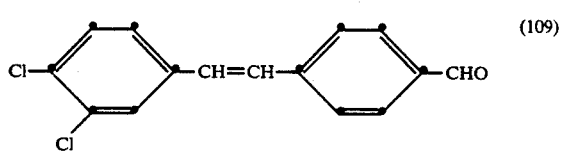
(109)

to a condensation reaction with diethyl p-methylsulfonylbenzylphosphonate in accordance with Example 1. The aldehyde of the formula (109) is prepared analogously to the aldehyde of the formula (102); it being also possible to employ an aqueous 50% solution of potassium hydroxide instead of solid potassium hydroxide. The crude product is purified, after clarification by hot filtration, by crystallization from ethanol: melting point 128°–136° C.

APPLICATION EXAMPLES

EXAMPLE 6

A polyester woven fabric (terylene type 540) is treated at 40° C. on a dyeing machine, at a liquor ratio of 1 to 20, with an aqueous bath containing 0.1% by weight of the fluorescent brightener of the formula 101 (Example 1) in a finely dispersed form and 1 g/l of a fatty alcohol polyglycol ether. The temperature is raised to 130° C. in the course of 30 minutes and is kept at this level for a further 30 minutes. The bath is then cooled again to 40° C. in the course of 15 minutes. The textile material is subjected to aftertreatment by being rinsed for 30 seconds in running demineralized water and being dried at 180° C. The polyester fabric which has been treated in this way exhibits a strong white effect.

EXAMPLE 7

The procedure described in Example 6 is repeated, using a fluorescent brightener of the formula 106 (Example 3) instead of that of the formula 101. Similarly, good white effects are obtained.

EXAMPLE 8

The procedure of Example 6 is repeated, using an equal amount of a fluorescent brightener composed of a binary mixture of 70% by weight of the compound of the formula 101 and 30% by weight of the compound of the formula 103 (Example 2), instead of the fluorescent brightener of the formula 101. Similarly, good white effects are obtained.

EXAMPLE 9

The procedure of Example 6 is repeated, using an equal amount of a fluorescent brightener composed of a ternary mixture the preparation of which is described in Example 2 and which consists of 38% by weight of the compound of the formula 101, 56% by weight of the compound of the formula 103 and 6% by weight of the compound of the formula 104, instead of the fluorescent brightener of the formula 101. Similarly, good white effects are obtained.

EXAMPLE 10

The procedure of Example 6 is repeated, using an equal amount of a fluorescent brightener composed of a binary mixture of 70% by weight of the compound of the formula 108 (Example 5) and 30% by weight of 1,4-di-(3,4-dichlorostyryl)-benzene, instead of the fluorescent brightener of the formula 101. Similarly, good white effects are obtained.

EXAMPLE 11

The procedure of Example 6 is repeated, using an equal amount of a fluorescent brightener composed of a ternary mixture of 32% by weight of the compound of the formula 108 (Example 5), 64% by weight of 1,4-di-(3,4-dichlorostyryl)-benzene and 4% by weight of the compound of the formula 104 (Example 2), instead of the fluorescent brightener of the formula 101. Similarly, good white effects are obtained.

EXAMPLE 12

A polyester woven fabric (terylene type 540) is padded at room temperature with an aqueous liquor containing 0.1 g/l of the fluorescent brightener of the formula 101 in a dispersed form and 1 ml/l of Invadin JFC 200% where Invadin is

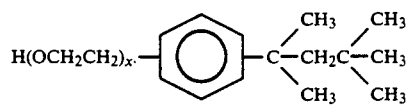

where the average value of X is 8.2. The pickup is 65%. The material is then dried for 30 minutes at a temperature of 80° C. and is subsequently thermofixed at 200° C. The polyester woven fabric which has been treated in this way exhibits a strong white effect.

The procedure described above is repeated, using a fluorescent brightener of the formula 108 (Example 5) or of the formula 106 (Example 3) instead of the fluorescent brightener of the formula 101. Similarly, good white effects are obtained.

The procedure described above is repeated, using in each case equal amounts of fluorescent brighteners composed of the binary and ternary mixtures such as are mentioned in relation to the exhaustion process in Examples 8 to 11, instead of the fluorescent brightener of the formula 101. Similarly, good white effects are also obtained using the pad-bake process.

We claim:

1. A 1,4-distyrylbenzene compound of formula

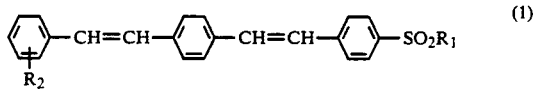

in which $R_1$ is $C_1$–$C_4$-alkyl and $R_2$ is 2-cyano.

2. A 1,4-distyrylbenzene compound according to claim 1 wherein $R_1$ is methyl or ethyl.

3. A 1,4-distyrylbenzene compound according to claim 2 wherein $R_1$ is methyl.

4. A mixture of a compound of formula 1 according to claim 1 with a compound of the formulae

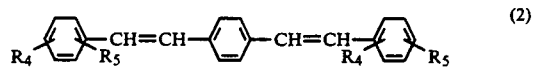

or

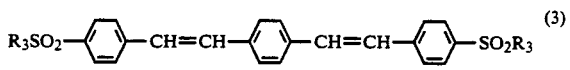

or a mixture thereof wherein $R_3$ is $C_1$–$C_4$-alkyl or phenyl, $R_4$ is cyano, $COOC_1$–$C_4$-alkyl or chlorine and $R_5$ is hydrogen or chlorine.

5. A mixture according to claim 4 containing 1 to 99% by weight of 1-(2-cyanostyryl)-4-(4-methylsulfonylstyryl)-benzene or 1-(2-cyanostyryl)-4-(4-ethylsulfonylstyryl)-benzene, 1 to 99% by weight of 1,4-di-(2-cyanostyryl)-benzene and 0 to 20% by weight of 1,4-di-(4-methylsulfonylstyryl)benzene or 1,4-di-(4-ethylsulfonylstyryl)-benzene.

6. A mixture of compounds according to claim 4 which further comprises an additional fluorescent brightener selected from the group consisting of 1,4-distyrylbenzenes, 4,4'-distyrylbiphenyls, 2,5-dibenzoxazolylthiophenes, 1,2-dibenzoxazolylethylenes, monobenzoxazolylstilbenes, monobenzoxazolylstyrenes, dibenzoxazolylstilbenes, dibenzoxazolylstyrenes, triazinylpyrenes, 4-triazolylstilbenes, isoxazolylstilbenes, dibenzoxazolylnaphthalenes, triazolylcoumarins, pyrazolyl-coumarins, phenylcoumarins, 4,4'-divinylstilbenes and naphthalimides.

7. A method for the fluorescent brightening of polyester fibers which comprises the step of applying to the polyester fibers a 1,4-distyrylbenzene compound of formula

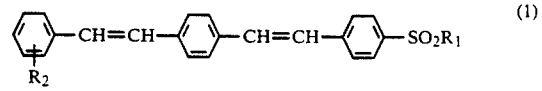

in which $R_1$ is $C_1$–$C_4$-alkyl and $R_2$ is 2-cyano.

* * * * *